United States Patent [19]

Criddle et al.

[11] Patent Number: 5,602,036
[45] Date of Patent: Feb. 11, 1997

[54] METHOD AND COMPOSITIONS FOR REMEDIATION

[75] Inventors: Craig S. Criddle, Okemos; Gregory M. Tatara; Michael J. Dybas, both of Lansing, all of Mich.

[73] Assignee: Board of Trustees operating Michigan State University, East Lansing, Mich.

[21] Appl. No.: 480,536

[22] Filed: Jun. 7, 1995

Related U.S. Application Data

[63] Continuation of Ser. No. 246,621, May 20, 1994, abandoned, which is a continuation-in-part of Ser. No. 62,072, May 14, 1993, abandoned.

[51] Int. Cl.$^6$ ................................................. C12S 1/00
[52] U.S. Cl. .................. 435/262; 435/252.1; 435/262.5; 435/874
[58] Field of Search ............................. 435/262, 262.5, 435/874, 252.1; 210/60

[56] References Cited

U.S. PATENT DOCUMENTS 4,479,936  10/1984  Vanderbergh et al. ................ 424/92
4,713,343  12/1987  Wilson et al. ......................... 435/264

OTHER PUBLICATIONS

Lewis et al. "Physiological Factors Affecting Carbon Tetrachloride Dehalogenation by Denitrifying Bacterium Pseudomonas sp. Strain KC" Applied and Environmental Microbiology, vol. 59, No. 5, May 1993, pp. 1635–1641.

Criddle, C. S., et al in Applied and Env. Microbiology vol. 56(11), 3240–3246 (1990).

Tatara, G. T., et al vol. 59(7), 2126–2131 (Jul. 1993).

Primary Examiner—Helen Pratt
Attorney, Agent, or Firm—Ian C. McLeod

[57] ABSTRACT

A method and compositions using a metabolite(s) produced by Pseudomonas KC (DSM 7136) to degrade aliphatic halogenated hydrocarbons. The metabolite(s) is used with an enabling microorganism to degrade the aliphatic halogenated hydrocarbons. The method and compositions are particularly useful with aquifer solutions and soils for removal of carbon tetrachloride.

17 Claims, 7 Drawing Sheets

METHOD AND COMPOSITIONS FOR REMEDIATION

CROSS-REFERENCE TO RELATED APPLICATION

The present application is a file wrapper continuation Ser. No. 08/246,621, filed May 5, 1994, now abandoned, which is a continuation-in-part of Ser. No. 08/062,072, filed May 14, 1993, now abandoned.

BACKGROUND OF THE INVENTION

(1) Field of the Invention

The present invention relates to a novel method and compositions for the degradation of aliphatic halogenated hydrocarbons into carbon dioxide or other harmless products by the use of a Pseudomonas metabolite(s) and microbial cells. In particular, the present invention relates to the degradation of carbon tetrachloride into carbon dioxide or other harmless products using the metabolite(s). The degradation can be accomplished in various defined media and also in the environment, particularly in contaminated aquifer solutions and soil.

(2) Description of Related Art

The ability of a wide variety of microorganisms to dehalogenate various compounds such as carbon tetrachloride (CT) is well known, and it has been demonstrated that this ability can be exploited for the remediation of contaminated water, waste streams, soil, and air. Typically, microbial CT transformations produce chloroform, which is even more persistent than CT and also poses health and cancer risks. Therefore, remediation strategies that avoid chloroform production are advantageous.

Previous nonbiological strategies for the remediation of sites contaminated with CT involve the extraction of groundwater coupled with above ground treatment by air stripping or adsorption to activated carbon. Air stripping uses large volumes of air to flush and dilute carbon tetrachloride and other volatile compounds out of water, while adsorption of organic contaminants to activated carbon binds the contaminant to a solid material for future disposal. These methods simply transfer carbon tetrachloride from one medium to another without destroying the contaminant.

Previous biological technologies include the stimulation of the indigenous microorganisms at a site to remove the contaminant. The advantage of this technology is the organisms are already adapted to the site and there are no problems associated with the delivery of a microorganism to the site. However, a disadvantage of this technology is that the organisms present may not be capable of degrading the contaminant or undesirable end products may result from the transformation. Another possibility involves augmenting the site with an organism that has been demonstrated to destroy the contaminant of interest under laboratory conditions. The advantage of this method is the organism and the mechanism of transformation can be understood and therefore modulated. However, the disadvantage of this technology is that the fate of the microorganism at the site is unknown. Typically, the introduced organism is incapable of competing with indigenous organisms, and colonization of the site by this introduced organism may be unobtainable.

The prior art has described the use of bacteria to biodegrade various compounds, particularly aliphatic halogenated hydrocarbons such as carbon tetrachloride. Thus, one of the herein listed inventors, Criddle, C. S., et al in Applied and Env. Microbiology 56, 3240–3246 (1990) describe the use of Pseudomonas KC for this purpose in axenic cultures without identifying the particular strain by deposit number. Application Ser. No. 08/062,072, now abandoned, describes the use of Pseudomonas KC under alkaline conditions to facilitate the growth of this bacterium over those present in the environment. This research is also described by Tatara, G. M., et al 59, 2126–2131 (July 1993) along with a discussion of the results with those metals.

OBJECTS

It is therefore an object of the present invention to provide a novel metabolite(s) which is produced by Pseudomonas KC and which functions with microorganisms to cause the decomposition of aliphatic halogenated hydrocarbon. Further, it is an object of the present invention to provide novel methods and compositions using the metabolite(s). Further still it is an object of the present invention to provide methods and compositions which are inexpensive to produce and use and which are very effective. These and other objects will become increasingly apparent by reference to the following description and the drawings.

DESCRIPTION OF PREFERRED EMBODIMENTS

Figure 1:
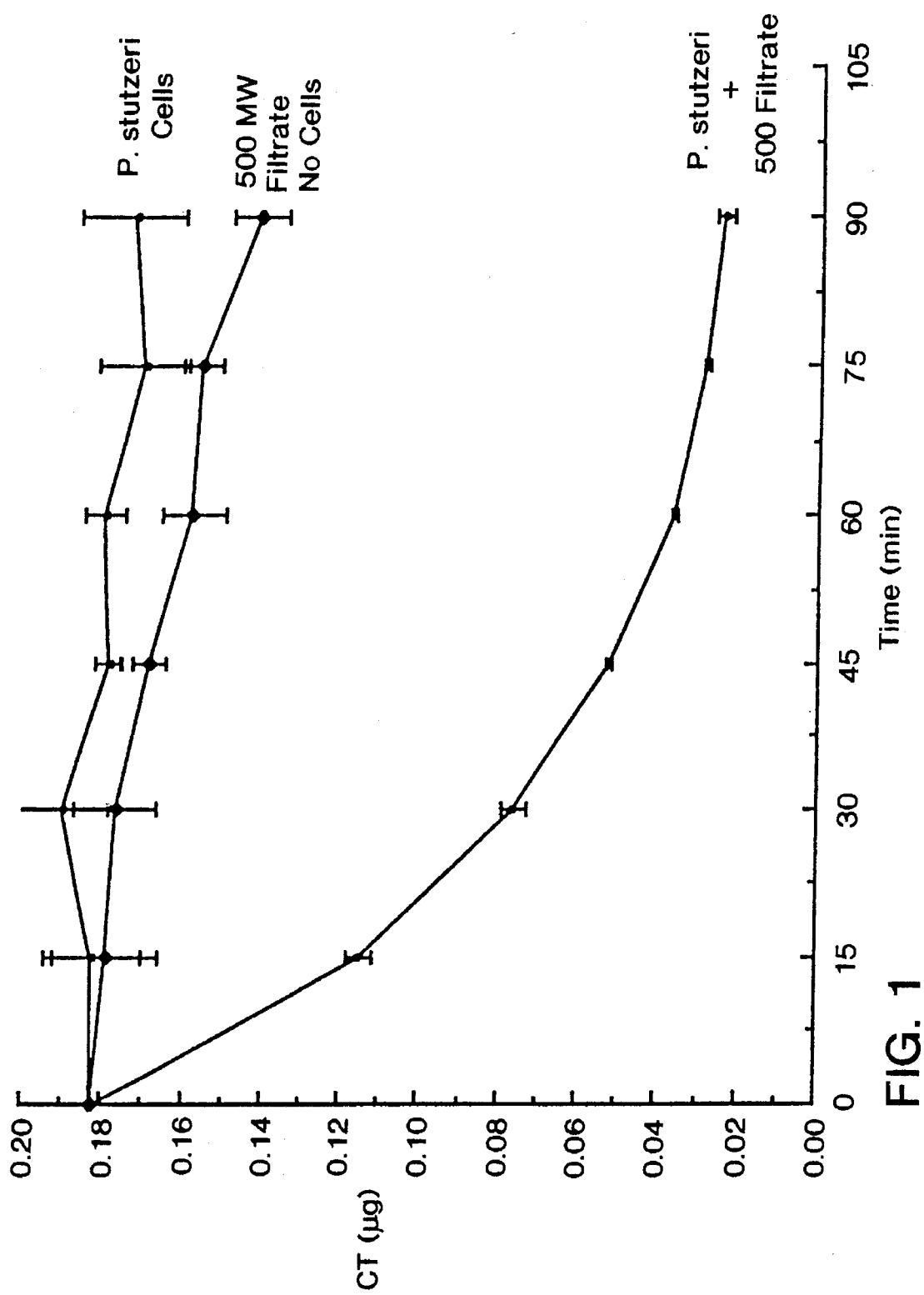
FIG. 1 is a graph showing the reconstitution of *Pseudomonas stutzeri* cells with Pseudomonas KC culture supernatant passed through a 500 molecular weight cut-off filter results in rapid CT degradation. Error bars represent the standard deviation of triplicate samples.

The present invention relates to an improvement in a method for degradation of an aliphatic halogenated hydrocarbon, the improvement which comprises: an extracellular metabolite(s) produced by Pseudomonas KC DSM 7136 in a growth medium into a material containing the aliphatic halogenated hydrocarbon and indigenous or added microorganisms; and degrading the halogenated hydrocarbon to produce carbon dioxide and other harmless end products.

Further, the present invention relates to an extracellular metabolite(s) having an apparent molecular weight of less than 500 produced by cells of Pseudomonas KC DSM 7136 in a growth medium in which the metabolite is soluble and secreted by the cells.

Further still, the present invention relates to a method for producing an extracellular metabolite(s) which comprises: growing cells of a Pseudomonas sp. in a growth medium which produces the metabolite of Pseudomonas KC DSM 7136 having an apparent molecular weight of less than 500; and isolating the metabolite from the cells.

The present invention also relates to a composition which comprises: an extracellular metabolite(s) having an apparent molecular weight of less than 500 produced by cells of Pseudomonas KC DSM 7136 in a growth medium in which the metabolite(s) is produced; and cells of an enabling microorganism, wherein the composition decomposes the aliphatic halogenated hydrocarbon to produce carbon dioxide and other harmless end products.

Finally, the present invention relates to a composition which comprises: an extracellular metabolite(s) having an apparent molecular weight of less than 500 produced by cells of Pseudomonas KC DSM 7136 in a growth medium in which the metabolite(s) is soluble and isolated from the cells; and an environmentally safe carrier which is non-toxic to an enabling microorganism which degrades aliphatic halogenated hydrocarbons in the presence of the metabolite.

The Pseudomonas strain KC is deposited as DSM 7136 with the Deutsche Sammlung von Mikroorganismen Und Zellkulturen GmbH, Mascherodor Weg I b, D-3300 Braunschweig, Germany. It is available upon request by deposit number and name.

The metabolite has an apparent molecular weight of less than 500. It is further characterized by the ability to transform CT in the presence of bacterial species other than Pseudomonas KC.

At least about $10^6$ cells per gram of the enabling cells are reconstituted with the metabolite containing medium. Preferably the cells are concentrated to between $10^9$ and $10^{12}$ cells per gram with removal of the culture media which may inhibit the metabolite(s).

The growth medium to produce the metabolite(s) is that typically used for Pseudomonas, including a nitrogen source, a carbon source, inorganic phosphate salt source, inorganic sulfur salt source, electron donor, electron acceptor and trace minerals. The pH of the preferred growth medium is adjusted to 7.8 to 8.2 and contains acetate and nitrate. The ratios of the active ingredients can vary in wide ranges, however, preferred are:

Acetate→800–5,000 mg/L
Nitrate→800–5,000 mg/L
pH→7.8–8.2
Phosphate→100–3,000 mg/L
Sulphate→100–1,000 mg/L A suitable medium is also used for the growth of the enabling cells.

Preferred enabling cells are bacteria of the genus Pseudomonas, Bacillus, and Escherichia. Particularly preferred are Pseudomonas species.

The aliphatic halogenated hydrocarbons include polyhalogenated molecules such as carbon tetrachloride (CT). They can also be present with aliphatic and aromatic hydrocarbons which can be degraded by various microorganisms.

The preferred method of this invention uses a supernatant factor(s) secreted by Pseudomonas sp. strain KC for the degradation of CT and other halogenated aliphatic compounds in the presence of diverse cell types. The method provides a means of CT transformation to carbon dioxide or other harmless end products without the production of chloroform using a factor(s) secreted by Pseudomonas sp. strain KC. Use of this factor(s) as disclosed herein has the advantage of biostimulation in that indigenous microorganisms may be used to transform CT without the need for introduction of an organism capable of surviving and competing with the indigenous organisms. The current invention also provides the advantage of bioaugmentation in that the secreted factor(s), its transformation products, and stability can be studied in the laboratory. Therefore, the advantages of both biostimulation and bioaugmentation are achieved without the disadvantages associated with these technologies. The present invention is particularly used where treatment and effective remediation of a CT contaminated site are of interest. Furthermore, it is used in situations where the end products from biostimulation are undesirable or bioaugmentation is impractical.

Pseudomonas KC produces a small (<500 MW) secreted factor(s) that is required for CT transformation by this organism. Both a physiologically active bacterial cell and this secreted factor(s) are required for CT transformation. This is based on the finding that CT transformation activity is obtained when diverse cell types other than Pseudomonas KC are combined with the secreted factor(s) required for dehalogenation. In the absence of the secreted factor, these cells are unable to transform CT to carbon dioxide or other harmless end products, or they do so slowly.

EXAMPLE 1

The present example involves growing Pseudomonas KC under denitrifying and iron limiting conditions to induce the ability to transform CT (Criddle, C. S., et al., Appl. Environ. Microbiol. 56, 3240–3246 (1990); and Tatara, G. M., et al., Appl. Environ. Microbiol. 59, 2126–2131 (1993)) Pseudomonas KC cells were grown in medium D, containing (per liter of degassed water) 2.0 g of $KH_2PO_4$, 3.5 g of $K_2HPO_4$, 1.0 g of $(NH_4)_2SO_4$, 0.5 g of $MgSO_4.7H_2O$, 1 ml of trace nutrient stock TN2, 1 ml of 0.15M $Ca(NO_3)_2$, 3.0 g of sodium acetate, and 2.0 g of sodium nitrate. Some experiments used different levels of acetate and nitrate. The pH of medium D was 7.0, but in the standard protocol it was adjusted to 8.0 with 3N KOH before autoclaving. This adjustment caused a white precipitate to form, and a precipitate remained after autoclaving.

Trace nutrient stock solution TN2 contained (per liter of deionized water) 1.36 g of $FeSO_4.7H_2O$, 0.24 g of $Na_2MoO_4. 2H_2O$, 0.25 g of $CuSO_4. 5H_2O$, 0.58 g of $ZnSO_4.7H_2O$, 0.29 g of $Co(NO_3)_2. 6H_2O$, 0.11 g of $NiSO_4.6H_2O$, 35 mg of $Na_2SeO_3$, 62 mg of $B_3(OH)_3$, 0.12 g of $NH_4VO_3$, 1.01 g of $MnSO_4.H_2O$, and 1 ml of $H_2SO_4$ (concentrated). Trace nutrient stock solution TN3 contained (per liter) 3.0 g of $FeSO_4.7H_2O$, 0.03 g of $Na_2MoO_4. 2H_2O$, 0.20 g of $ZnSO_4.7H_2O$, 0.05 g of $Co(NO_3)_2.6H_2O$, 0.02 g of $NiCl_2.6H_2O$, 20 mg of $B_3(OH)_3$, and 25 mg of $MnSO_4.H_2O$.

Media were prepared in 1- or 2-liter flasks, degassed for 30 to 60 min under vacuum to remove traces of chloroform, and transferred to a Coy anaerobic glove box (Coy Laboratory Products, Ann Arbor, Mich.) for dispensing. The glove box had an atmosphere of 10% hydrogen-90% nitrogen. Initial enrichments were prepared in 160-ml serum bottles containing 100 ml of medium D and sealed with Mininert valves (individually pressure tested) equipped with a compression O ring to close off the throat of the serum bottle. The medium was then autoclaved for 20 minutes at 121° C., cooled, and transferred back to the glove box. A few grams of aquifer material was added, the bottles were resealed and removed from the glove box, and CT from a sterile stock solution was added to give a liquid phase concentration of 100 to 200 µg/liter. The side-port needles (Alltech catalog no. 943052) used for sampling the gas phase were autoclaved prior to use. An actively transforming culture is centrifuged and filtered to remove cells from the culture supernatant. A fraction of the culture supernatant containing a low molecular weight secreted factor(s) required for dehalogenation is obtained. *Pseudomonas stutzeri* (courtesy of Harry Ridgeway, Orange County Water District, Fountain Valley, Calif.) cells were grown aerobically in Medium D (Criddle, C. S., et al., Appl. Environ. Microbiol. 56, 3240–3246 (1990); and Tatara, G. M., et al., Appl. Environ. Microbiol. 59, 2126–2131 (1993)) containing (per liter of deionized water) 2.0 g of $KH_2PO_4$, 3.5 g of $K_2HPO_4$, 1.0 g of $(NH_4)_2SO_4$, 0.5 g of $MgSO_4 \cdot 7H_2O$, 1 milliliter of trace nutrient stock TN2, 1 milliliter of 0.15M $Ca(NO_3)_2$, 3.0 g of sodium acetate, and 2.0 g of sodium nitrate. Medium D was prepared with trace nutrient stock solution TN2. Stock solution TN2 contained (per liter of deionized water) 1.36 g of $FeSO_4 \cdot 7H_2O$, 0.24 g of $Na_2MoO_4 \cdot 2H_2O$, 0.25 g of $CuSO_4 \cdot 5H_2O$, 0.58 g of $ZnSO_4 \cdot 7H_2O$, 0.29 g of $Co(NO_3)_2 \cdot 6H_2O$, 0.11 g of $NiSO_4 \cdot 6H_2O$, 35 mg of $Na_2SeO_3$, 62 mg of $H_3BO_3$, 0.12 g of $NH_4VO_3$, 1.01 g of $MnSO_4 \cdot H_2O$, and 1 ml of $H_2SO_4$ (concentrated). After addition of all essential media components, medium D was adjusted to a desired initial pH of 8.0 or 8.2 with 3N KOH. This final adjustment in pH resulted in the formation of a white precipitate. The resulting medium was autoclaved at 121° C. for 30 minutes.

Cultures of *Pseudomonas stutzeri* were centrifuged and the supernatant decanted. The resulting cell pellet was then resuspended in anoxic Medium D at 10× the original concentration. Resuspended *Pseudomonas stutzeri* cells were added to filtered Pseudomonas KC supernatant and CT transformation was monitored by gas chromatography.

Reconstitution of *Pseudomonas stutzeri* cells with culture filtrate from Pseudomonas KC resulted in rapid CT transformation to carbon dioxide. Neither *Pseudomonas stutzeri* cells nor culture filtrate from Pseudomonas KC were capable of significant transformation separately, but upon combination of these two fractions, rapid CT transformation activity was obtained as shown in FIG. 1.

EXAMPLE 2

The present example involves growing Pseudomonas KC under denitrifying and iron limiting conditions to induce the ability to transform CT (Criddle, C. S., et al., Appl. Environ. Microbiol. 56, 3240–3246 (1990); and Tatara, G. M., et al., Appl. Environ. Microbiol. 59, 2126–2131 (1993)). An actively transforming culture was centrifuged and filtered to remove cells from the culture supernatant. A fraction of the culture supernatant containing a low molecular weight secreted factor required for dehalogenation was obtained. *Pseudomonas fluorescens* (ATCC 13525) cells were grown aerobically in Medium D. Cultures of *Pseudomonas fluorescens* were centrifuged and the supernatant decanted. The resulting cell pellet was then resuspended in anoxic Medium D at 10× the original concentration. Resuspended *Pseudomonas fluorescens* cells were added to filtered Pseudomonas KC supernatant and CT transformation was monitored by gas chromatography.

Figure 2:
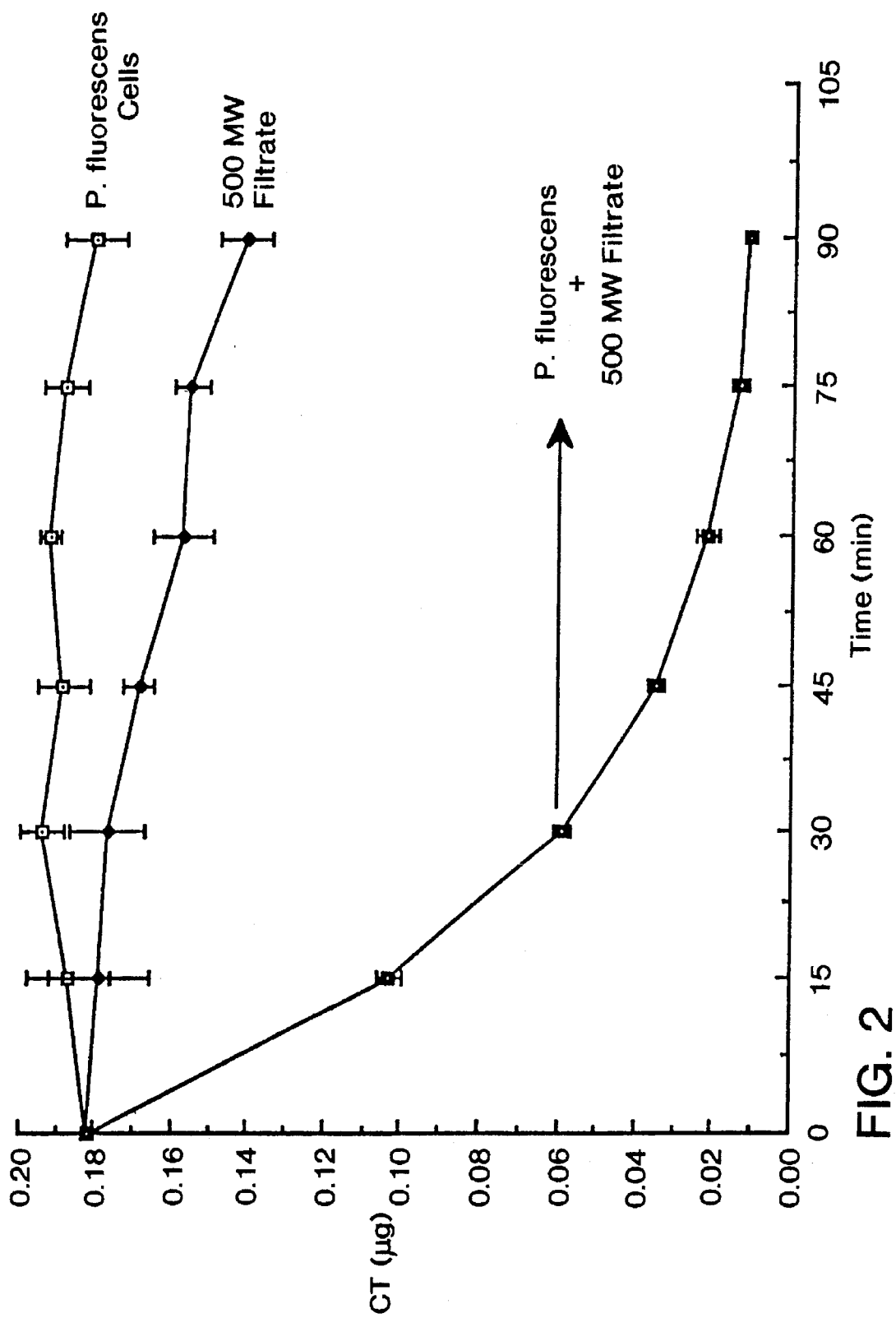
FIG. 2 is a graph showing that reconstitution of *Pseudomonas fluorescens* cells with Pseudomonas KC culture supernatant passed through a 500 molecular weight cut-off filter results in rapid CT degradation. Error bars represent the standard deviation of triplicate samples.

Reconstitution of *Pseudomonas fluorescens* cells with culture filtrate from Pseudomonas KC resulted in rapid CT transformation. Neither *Pseudomonas fluorescens* cells nor culture filtrate from Pseudomonas KC were capable of significant transformation separately, but upon combination of these two fractions, rapid CT transformation activity was obtained as shown in FIG. 2.

EXAMPLE 3

The present example involves growing Pseudomonas KC under denitrifying and iron limiting conditions to induce the ability to transform CT (Criddle, C. S., et al., Appl. Environ. Microbiol. 56, 3240–3246 (1990); and Tatara, G. M., et al., Appl. Environ. Microbiol. 59, 2126–2131 (1993)). An actively transforming culture was centrifuged and filtered to remove cells from the culture supernatant. A fraction of the culture supernatant containing a low molecular weight secreted factor(s) required for dehalogenation was obtained. *Escherichia coli* (ATCC 10798) cells were grown aerobically in modified Medium D substituting glucose for acetate as the electron donor. Cultures of *Escherichia coli* were centrifuged and the supernatant decanted. The resulting cell pellet was resuspended in anoxic modified Medium D at 10× the original concentration. Washed *Escherichia coli* cells were added to filtered Pseudomonas KC supernatant and CT transformation was monitored by gas chromatography.

Figure 3:
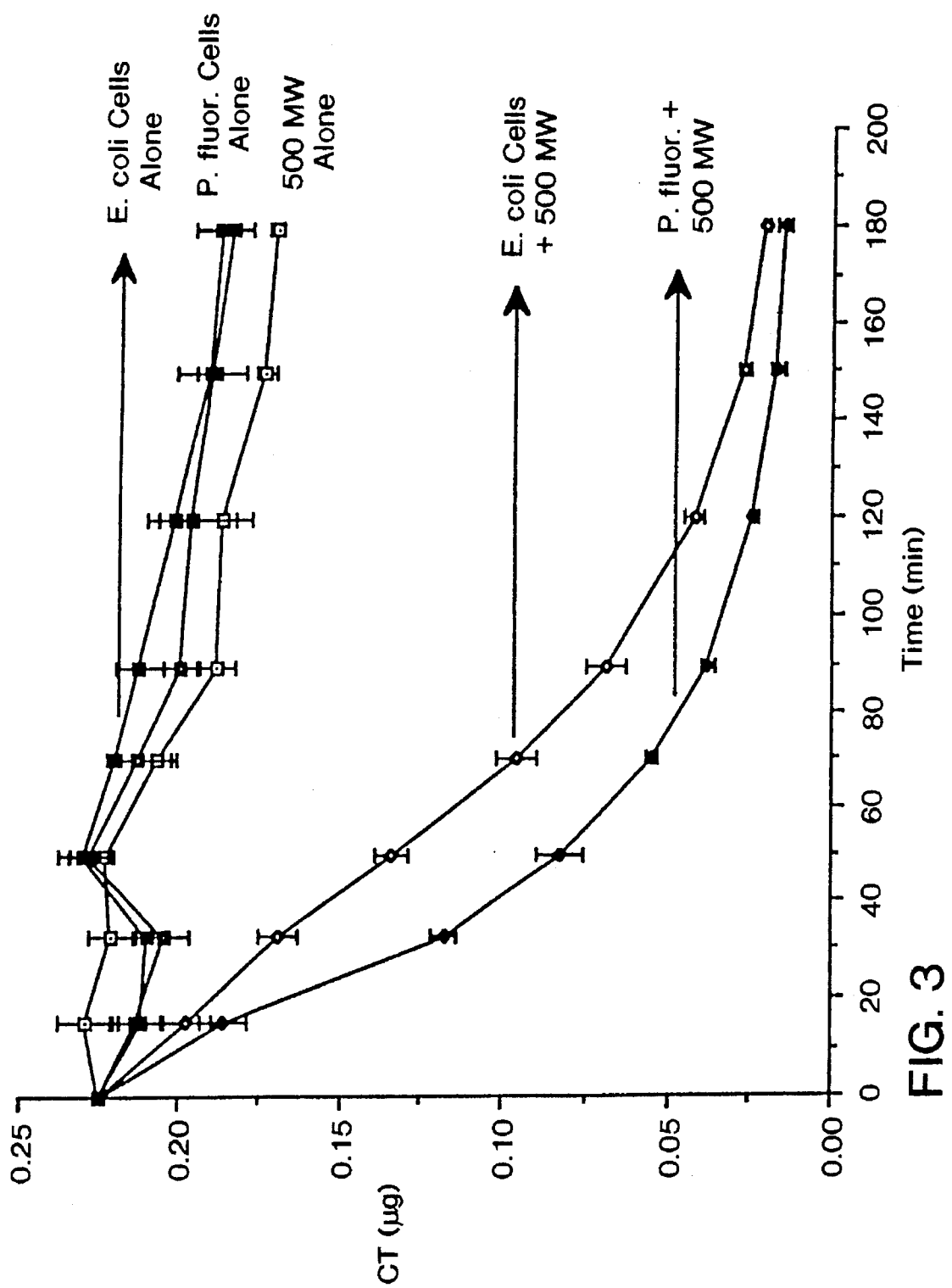
FIG. 3 is a graph showing that reconstitution of *Escherichia coli* cells with Pseudomonas KC culture supernatant passed through a 500 molecular weight cut-off filter results in rapid CT transformation. Error bars represent the standard deviation of triplicate samples.

Reconstitution of *Escherichia coli* cells with culture filtrate from Pseudomonas KC resulted in rapid CT transformation. Neither *Escherichia coli* cells nor culture filtrate from Pseudomonas KC was capable of significant transformation separately, but upon combination of these two fractions, rapid CT transformation activity was obtained as shown in FIG. 3.

EXAMPLE 4

The present example involves growing Pseudomonas KC under denitrifying and iron limiting conditions to induce the ability to transform CT (Criddle, C. S., et al., Appl. Environ. Microbiol. 56, 3240–3246 (1990); and Tatara, G. M., et al., Appl. Environ. Microbiol. 59, 2126–2131 (1993)). An actively transforming culture was centrifuged and filtered to remove cells from the culture supernatant. A fraction of the culture supernatant containing a low molecular weight secreted factor(s) required for dehalogenation was obtained. *Bacillus subtilus* (ATCC 6051), a known gram positive organism, was grown aerobically in Nutrient Broth (Difco Co., Detroit, Mich.). Cultures of *Bacillus subtilus* were centrifuged and the supernatant decanted. The resulting cell pellets were resuspended in anoxic modified Medium D at 10× their original concentration. Resuspended *Bacillus subtilus* cells were added to filtered Pseudomonas KC supernatant and CT transformation was monitored by gas chromatography.

Figure 4:
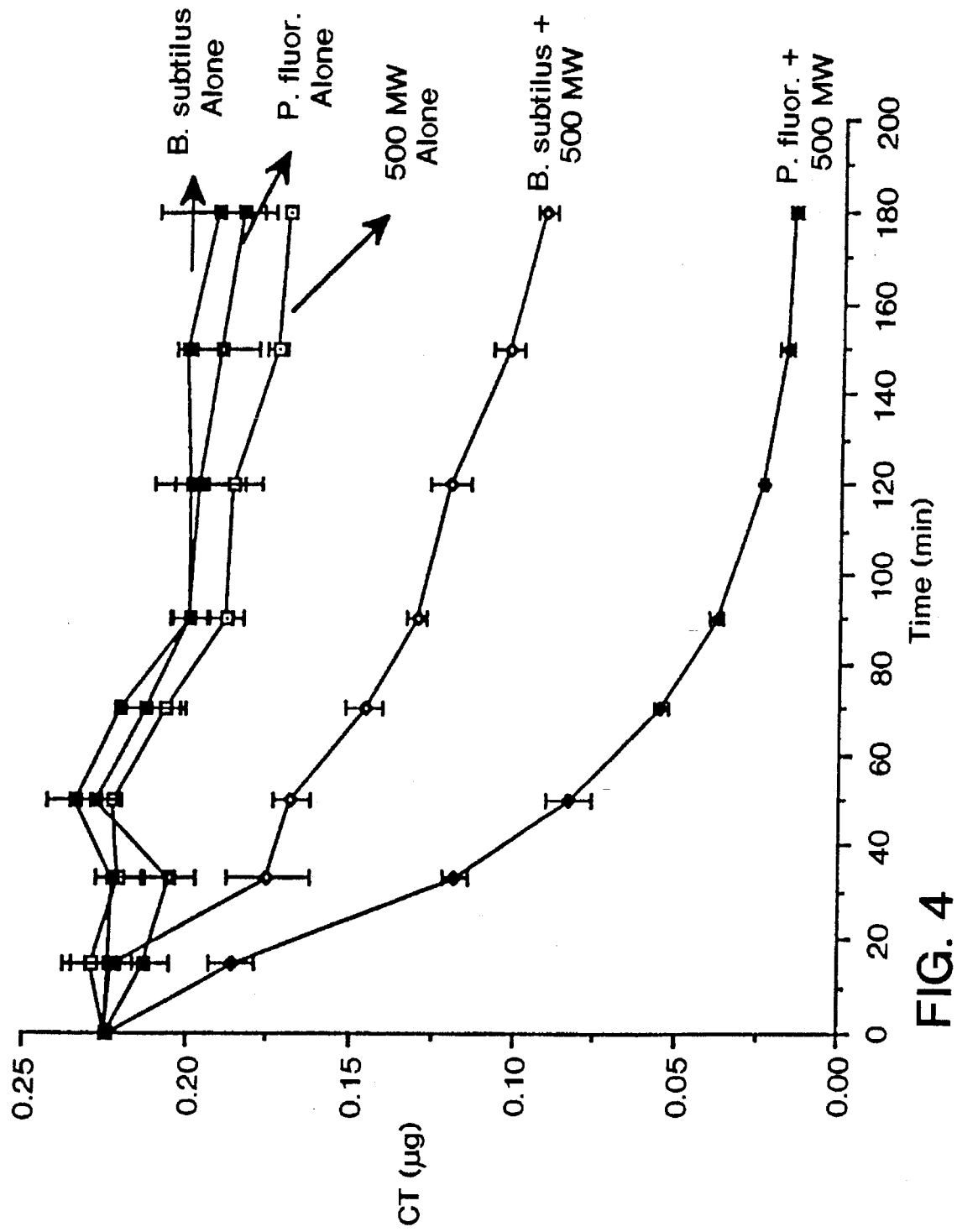
FIG. 4 is a graph showing that reconstitution of *Bacillus subtilus* cells with Pseudomonas KC culture passed through a 500 molecular weight cut-off filter results in CT transformation. The transformation with gram positive *Bacillus subtilus* is not as rapid as with gram negative *Pseudomonas fluorescens*. Error bars represent the standard deviation of triplicate samples.

Reconstitution of *Bacillus subtilus* cells with culture filtrate from Pseudomonas KC resulted in CT transformation. Neither *Bacillus subtilus* cells nor culture filtrate from Pseudomonas KC was capable of significant transformation separately, but upon combination of these two fractions, CT transformation activity was obtained as shown in FIG. 4.

EXAMPLE 5

The present example involves growing Pseudomonas KC under denitrifying and iron limiting conditions to induce the ability to transform CT (Criddle, C. S., et al., Appl. Environ. Microbiol. 56, 3240–3246 (1990); and Tatara, G. M., et al., Appl. Environ. Microbiol. 59, 2126–2131 (1993)). An actively transforming culture was centrifuged and filtered to remove cells from the culture supernatant. A fraction of the culture supernatant containing a low molecular weight secreted factor(s) required for dehalogenation was obtained. A consortium of microorganisms obtained from an aquifer in Schoolcraft, Michigan was grown aerobically in pH 7 Medium D supplemented with 10 μM iron sulfate. Cultures of Schoolcraft consortium were centrifuged and the supernatant decanted. The resulting cell pellet was then resuspended in anoxic Medium D at 10× the original concentration. Washed Schoolcraft cells were added to filtered Pseudomonas KC supernatant and CT transformation was monitored by gas chromatography.

Figure 5:
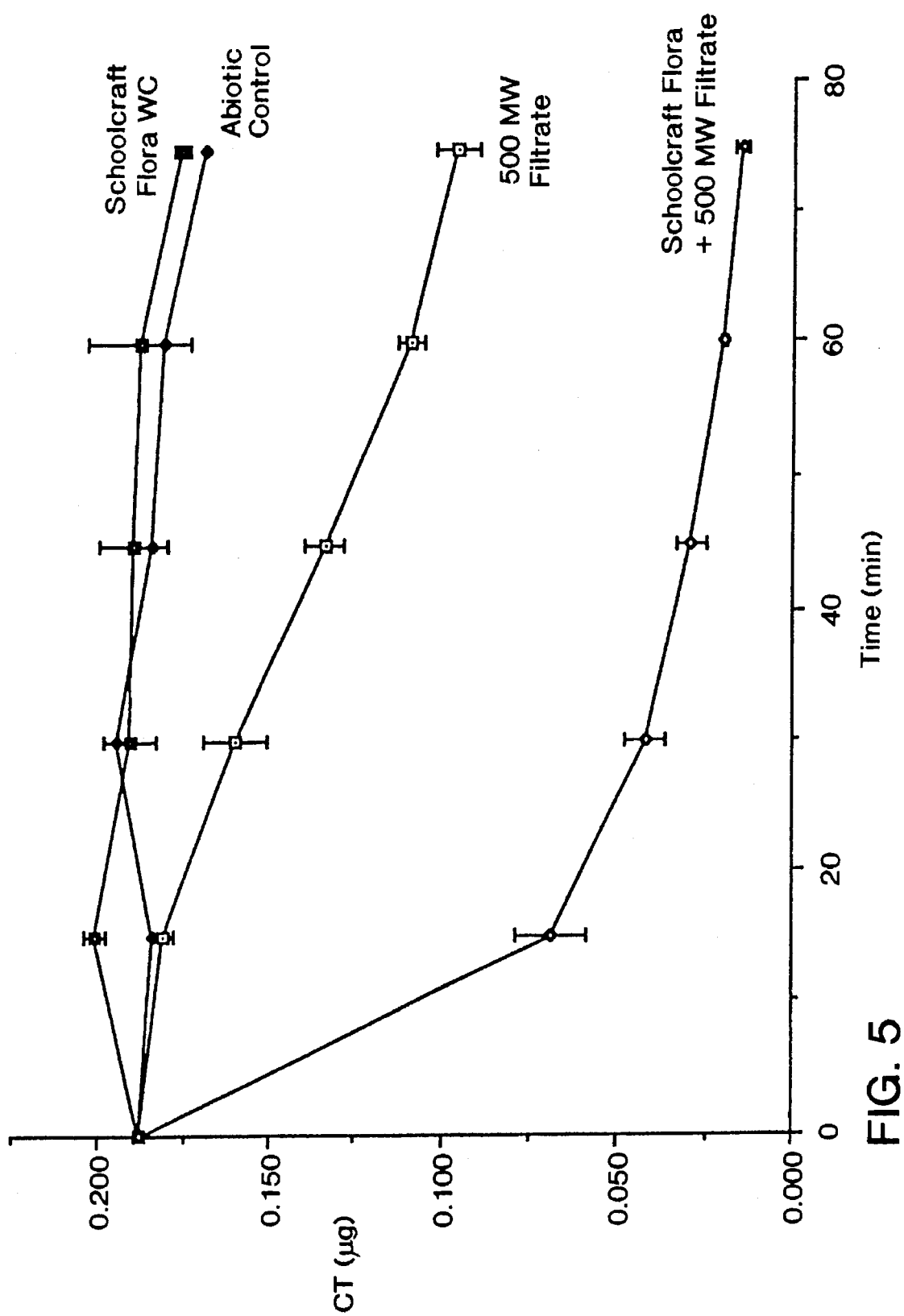
FIG. 5 is a graph showing that reconstitution of a Schoolcraft, Mich. site consortia with Pseudomonas KC culture supernatant passed through a 500 molecular weight cut-off filter results in rapid CT degradation. Error bars represent the standard deviation of triplicate samples.

Reconstitution of Schoolcraft consortium cells with culture filtrate from Pseudomonas KC resulted in rapid CT transformation. Neither Schoolcraft consortia nor culture filtrate from Pseudomonas KC was capable of significant transformation separately, but upon combination of these two fractions, rapid CT transformation activity was obtained as shown in FIG. 5.

EXAMPLE 6

The present example involves growing Pseudomonas KC in Hanford, Wash. synthetic groundwater medium (SGM). SGM contained per liter of deionized water 0.455 g of $Na_2SiO_3 \cdot 9 H_2O$, 0.16 g $Na_2CO_3$, 0.006 g of $Na_2SO_4$, 0.02 g of KOH, 0.118 g of $MgCl_2 \cdot 6H_2O$, 0.0081 g of $CaCl_2 \cdot 2H_2O$, 13.61 g of $KH_2PO_4$, 1.6 g of NaOH, 1.6 g of $NaNO_3$, 1.6 g of acetic acid and 1 mL of trace element solution. The trace element solution contained per liter of deionized water 0.021 g of $LiCl_2$, 0.08 g of $CuSO_4 \cdot 5H_2O$, 0.106 g of $ZnSO_4 \cdot 7H_2O$, 0.6 g of $H_3BO_3$, 0.123 g of $Al_2(SO_4)_3 \cdot 18 H_2O$, 0.11 g of $NiCl_2 \cdot 6 H_2O$, 0.109 g of $CoSO_4 \cdot 7H_2O$, 0.06 g of $TiCl_4$, 0.03 g of KBr, 0.03 g of KI, 0.629 g of $MnCl_2 \cdot 4H_2O$, 0.036 g of $SnCl_2 \cdot 2H_2O$, 0.3 g of $FeSO_4 \cdot 7H_2O$. For the growth of Pseudomonas KC, SGM medium was pH adjusted to 8.2 with 3N KOH prior to autoclaving.

An actively transforming culture of Pseudomonas KC grown in SGM was centrifuged and filtered to remove cells from the culture supernatant. A fraction of the culture supernatant containing a low molecular weight secreted factor(s) required for dehalogenation was obtained. A consortium of microorganisms (HC-14) obtained from an aquifer in Hanford, Wash. (courtesy of Battelle Pacific Northwest Laboratories, Richland, Wash.) was grown anoxically in SGM Medium at pH 7.5. Cultures of HC-14 were centrifuged and the supernatant decanted. The resulting cell pellet was then resuspended in anoxic SGM at 10× the original concentration. Washed HC-14 cells were added to filtered Pseudomonas KC supernatant and CT transformation was monitored by gas chromatography.

Figure 6:
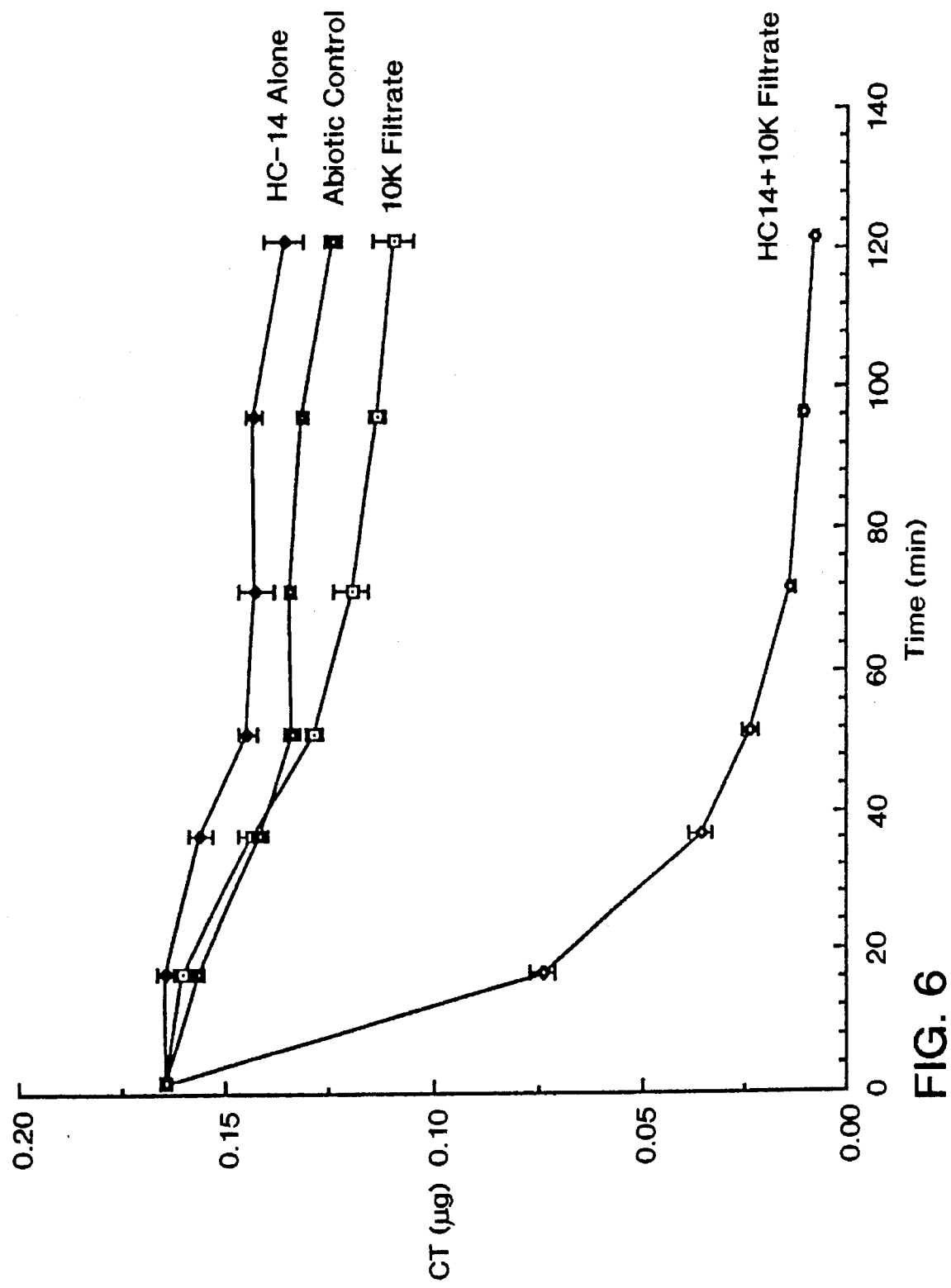
FIG. 6 is a graph showing that reconstitution of a Hanford, Wash. site consortium (HC-14) with Pseudomonas KC culture supernatant passed through a 10,000 molecular weight cut-off filter results in rapid CT transformation. Error bars represent the standard deviation of triplicate samples.

Reconstitution of HC-14 cells with culture filtrate from Pseudomonas KC resulted in rapid CT transformation. Neither HC-14 cells nor culture filtrate from Pseudomonas KC was capable of significant transformation separately, but upon combination of these two fractions, rapid CT transformation activity was obtained as shown in FIG. 6.

EXAMPLE 7

The present example involves the transformation of carbon tetrachloride in Hanford Aquifer Solid Slurries. Approximately 2 g of Hanford aquifer solids were placed into 18 sterile aluminum seal tubes. Each tube received 2mL of SGM medium (pH 8.2) without acetate. Six tubes were autoclaved as sterile controls, and six tubes received acetate at a final concentration of 800 mg/L. The tubes were then spiked with 0.5 μg of CT and shaken at room temperature. After three days, the tubes that received acetate received an additional spike of acetate and nitrate at a final concentration of 800 mg/L for each. Two days later, an actively transforming culture of Pseudomonas KC grown in SGM was centrifuged and filtered to remove cells from the culture supernatant. A fraction of the culture supernatant containing a low molecular weight secreted factor(s) required for dehalogenation was obtained. Tubes receiving the supernatant factor(s) involved in CT transformation were spiked with 2 ml of filtrate. Cultures not receiving the supernatant factor were spiked with 2 mL of anoxic SGM pH 8.2. Tubes were incubated for 48 hours at room temperature after which time they were heated to 70° C. to release solid bound CT, and CT mass was assayed by gas chromatography.

The addition of KC supernatant factor to acetate- and nitrate-stimulated indigenous flora in the soil slurry resulted in CT removal as shown in Table 1.

TABLE 1

| Transformation of Carbon Tetrachloride in Hanford Aquifer Solid Slurries | |
|---|---|
| Test Sample | Mass of CT Remaining after 48 hr. Incubation (μg)[a] |
| 1) Sterile Control | 0.451 ± 0.011[b] |
| 2) Sterile Control + KC Supernatant Factor | 0.453 ± 0.052 |
| 3) Indigenous Flora | 0.457 ± 0.029 |
| 4) Indigenous Flora + KC Supernatant Factor[c] | 0.435 ± 0.017 |
| 5) Stimulated Indigenous Flora[d] | 0.493 ± 0.046 |
| 6) Stimulated Indigenous Flora + KC Supernatant Factor | 0.343 ± 0.005 | a. An initial CT mass of 0.5 μg was added to all samples. Final CT mass was determined by heating to 0° C. to release solid bound CT.

b. ±values represent the standard deviation of three independent samples.

c. KC supernatant factor was added as 2 ml of 10,000 MW filtrate from an actively transforming culture of Pseudomonas sp. strain KC grown in SGM medium at pH 8.3.

d. Supplemented with two pulse additions of acetate and nitrate at a final concentration of 800 mg/L. No CT removal was observed: 1) in the sterile controls that received the KC supernatant factor; 2) by the indigenous flora; 3) by the indigenous flora that received KC supernatant factor; 4) by stimulated indigenous flora.

EXAMPLE 8

Figure 7:
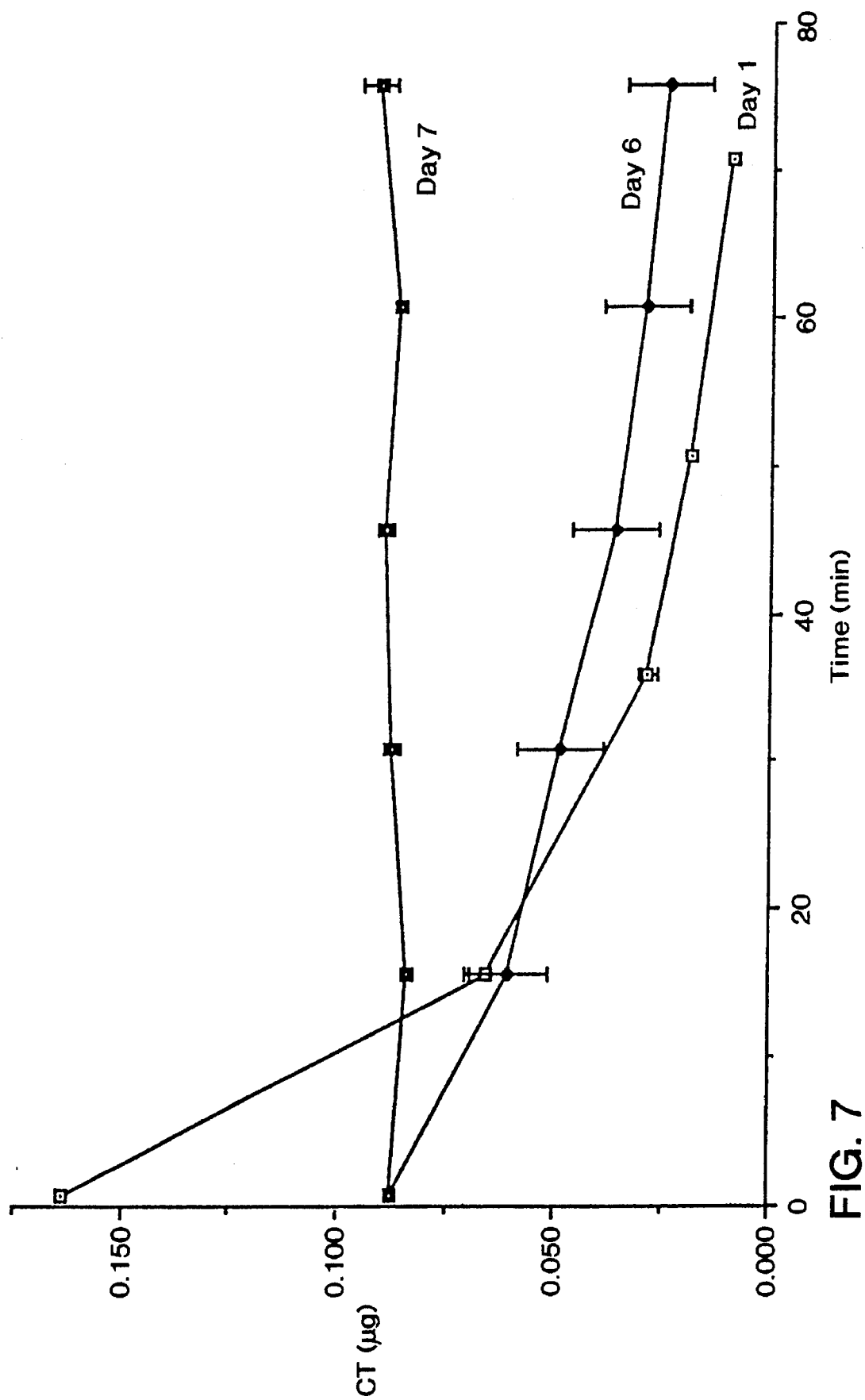
FIG. 7 is a graph showing the stability of KC supernatant factor responsible for dechlorination. Supernatant factor remained active for 6 days and lost activity on day 7. Supernatant factor was reconstituted with *Pseudomonas fluorescens* cells daily; only the first, sixth, and seventh day of the assay are illustrated. Error bars represent the standard deviation of triplicate samples.

The present example involves the stability of the secreted supernatant factor(s) produced by Pseudomonas KC. Pseudomonas KC was grown under denitrifying and iron limiting conditions in SGM medium at pH 8.2. An actively transforming culture is centrifuged and filtered to remove cells from the culture supernatant. A fraction of the culture supernatant containing a low molecular weight secreted factor(s) required for dehalogenation was obtained. Culture supernatant was stored in SGM at 16° C. (the actual temperature of Hanford groundwater in situ) under a headspace of nitrogen. *Pseudomonas fluorescens* cells were grown aerobically in Medium D. Cultures of *Pseudomonas fluorescens* were centrifuged and the resulting supernatant was decanted. Cell pellets were resuspended in anoxic Medium D at 10× their original concentration. Washed *Pseudomonas fluorescens* cells were added to filtered Pseudomonas KC supernatant and CT transformation was monitored by gas chromatography daily. FIG. 7 demonstrates the stability of the secreted factor after six days of storage in SGM at 16° C under a nitrogen headspace. Loss of activity was observed on day seven, indicating that the secreted factor has a finite stability of six days under the indicated storage conditions.

EXAMPLE 9

The present example involves the stability of freeze-dried culture filtrate from Pseudomonas KC. An actively transforming culture of Pseudomonas KC grown in SGM medium was centrifuged and filtered to remove cells from culture supernatant. A fraction of the culture supernatant containing a low molecular weight secreted factor required for dehalogenation was obtained by passing the culture filtrate through a 10,000 molecular weight (MW) cut-off filter. Culture filtrate was freeze-dried and then stored at −20° C. under aerobic conditions for six days. Culture filtrate was rehydrated (at 1× and 2× the original volume prior to freeze-drying) with deionized water under aerobic conditions and subsequently degassed to remove oxygen. *Pseudomonas fluorescens* cells were grown aerobically in Medium D. Cultures of *Pseudomonas fluorescens* were centrifuged and the resulting supernatant was decanted. Cell pellets were resuspended in anoxic medium D at 10× their original concentration. Resuspended *Pseudomonas fluorescens* cells were added to the rehydrated Pseudomonas KC supernatant and CT transformation was monitored by gas chromatography.

Reconstitution of *Pseudomonas fluorescens* cells with rehydrated freeze-dried culture filtrate resulted in rapid CT transformation. Samples were respiked with CT until final transformation capacity was reached. FIG. 8 demonstrated the increase in CT transformation capacity that was observed by concentrating the culture filtrate 2 fold and recombining with *Pseudomonas fluorescens* cells.

TABLE 2

Transformation of Carbon Tetrachloride by rehydrated culture filtrate from Pseudomonas KC reconstructed with *Pseudomonas fluorescens*

| Test Sample | Mass of CT Removed after 24 hours incubation (μg) |
|---|---|
| 1) *Pseudomonas fluorescens* | 0.080 ± 0.044 |
| 2) *Pseudomonas fluorescens* + 1X rehydrated culture filtrate[a] | 0.872 ± 0.025 |
| 3) *Pseudomonas fluorescens* + 2X rehydrated culture filtrate[b] | 0.993 ± 0.007 | a. 1× represents 10,000 MW culture filtrate that was rehydrated to its original volume prior to freeze-drying.

b. 2× represents 10,000 MW culture filtrate that was rehydrated to half the original sample volume for a 2-fold concentration increase.

It is intended that the foregoing description be only illustrative of the present invention and that the present invention be limited only to the hereinafter appended claims.

We claim:

1. In a method for anaerobic degradation of an aliphatic halogenated hydrocarbon the improvement which comprises:

(a) introducing extracellular metabolites produced by Pseudomonas KC DSM 7136 (ATCC 55595) in a first growth medium, wherein the growth medium contains a nitrogen source, a carbon source, an inorganic phosphate salt, an inorganic sulfur salt, an electron donor, an electron acceptor and trace minerals, and wherein the metabolites separated from the growth medium and separated from the Pseudomonas KC from the first growth medium when combined with *Pseudomonas fluorescens* ATCC 13525 produces degradation of carbon tetrachloride in a second growth medium containing the nitrogen source, the carbon source, the inorganic phosphate salt, the inorganic sulfur salt, the electron donor, the electron acceptor and the trace minerals wherein the metabolites are introduced into a material containing the aliphatic halogenated hydrocarbon and an indigenous or added bacterium other than the Pseudomonas KC which does not degrade the halogenated hydrocarbon to carbon dioxide and other end products, wherein the bacterium other than the Pseudomonas KC and the metabolites together can degrade the halogenated hydrocarbon to carbon dioxide and other end products and wherein the bacterium is a member selected from the group consisting of Pseudomonas, Bacillus and Escherichia and mixtures thereof; and (b) degrading the halogenated hydrocarbon with the bacterium to produce the carbon dioxide and the other end products.

2. The method of claim 1 wherein the bacterium is a Pseudomonas sp.

3. The method of claim 1 wherein the bacterium is an Escherichia sp.

4. The method of claim 1 wherein the bacterium is a Bacillus sp.

5. The method of claim 1 wherein the indigenous or added bacterium is in the material as a consortium of bacteria isolated from a site contaminated with the aliphatic halogenated hydrocarbon.

6. The method of claim 1 wherein the aliphatic halogenated hydrocarbon is carbon tetrachloride.

7. The method of claim 1 wherein prior to step (a) the bacterium other than the Pseudomonas KC is grown in a separate growth medium which is the same as the growth medium used for producing the metabolites from Pseudomonas KC.

8. A composition comprising isolated extracellular metabolites produced by cells of Pseudomonas KC DSM 7136 (ATCC 55595) in a first growth medium in which the metabolites are soluble wherein the first growth medium contains a nitrogen source, a carbon source, an inorganic phosphate salt, an inorganic sulfur salt, an electron donor, an electron acceptor and trace minerals, and wherein the metabolites separated from the growth medium and separated from the Pseudomonas KC from the first growth medium when combined with *Pseudomonas fluorescens* ATCC 13525 produces degradation of carbon tetrachloride in a second growth medium containing the nitrogen source, the carbon source, the inorganic phosphate salt, the inorganic sulfur salt, the electron donor, the electron acceptor and the trace minerals.

9. A method for producing extracellular metabolites which comprises:

(a) growing cells of Pseudomonas KC DSM 7136 to produce a metabolite in a growth medium, wherein the growth medium contains a nitrogen source, a carbon source, an inorganic phosphate salt, an inorganic sulfur salt, an electron donor, an electron acceptor and trace minerals, and wherein the metabolites separated from the growth medium and separated from the Pseudomonas KC from the first growth medium when combined with *Pseudomonas fluorescens* ATCC 13525 produces degradation of carbon tetrachloride in a second growth medium containing the nitrogen source, the carbon source, the inorganic phosphate salt, the inorganic sulfur salt, the electron donor, the electron acceptor and the trace minerals to produce the metabolites; and (b) isolating the metabolites from the cells.

10. A composition for degrading carbon tetrachloride to carbon dioxide and other end products, which comprises:

(a) extracellular metabolites having an apparent molecular weight of less than 500 produced by cells of Pseudomonas KC DSM 7136 in a first growth medium which provides for the growth of the metabolites wherein the growth medium contains a nitrogen source, a carbon source, an inorganic phosphate salt, an inorganic sulfur salt, an electron donor, an electron acceptor and trace minerals; and (b) cells of at least one bacterium other than the Pseudomonas KC selected from the group consisting of Pseudomonas, Bacillus and Escherichia and mixtures thereof which without the metabolite do not degrade the carbon tetrachloride to the carbon dioxide and the other end products, wherein the metabolites separated from the first growth medium and separated from the Pseudomonas KC when combined with *Pseudomonas fluorescens* ATCC 13525 produces degradation of carbon tetrachloride in a second growth medium containing the nitrogen source, the carbon source, the inorganic phosphate salt, the inorganic sulfur salt, the electron donor, the electron acceptor and the trace minerals.

11. The composition of claim 10 wherein the bacterium is a Pseudomonas sp.

12. The composition of claim 10 wherein the bacterium is *Escherichia coli*.

13. The composition of claim 10 wherein the bacterium is a Bacillus sp.

14. The composition of claim 10 wherein the bacterium is as a consortium of bacteria isolated from a site contaminated with the aliphatic halogenated hydrocarbon.

15. The composition of claim 10 wherein the cells of the bacterium other than the Pseudomonas KC are grown in a separate growth medium which is the same as the growth medium used for producing the metabolites from Pseudomonas KC.

16. A composition which comprises:

(a) extracellular metabolites having an apparent molecular weight of less than 500 produced by cells of Pseudomonas KC DSM 7136 in a first growth medium in which the metabolites are soluble, wherein the first growth medium contains a nitrogen source, a carbon source, an inorganic phosphate salt, an inorganic sulfur salt, an electron donor, an electron acceptor and trace minerals and wherein the metabolites separated from the growth medium and separated from the Pseudomonas KC from the first growth medium when combined with *Pseudomonas fluorescens* ATCC 13525 produces degradation of carbon tetrachloride in a second growth medium containing the nitrogen source, the carbon source, the inorganic phosphate salt, the inorganic sulfur salt, the electron donor, the electron acceptor and the trace minerals, wherein the metabolites are isolated from the cells; and (b) an environmentally safe carrier which is non-toxic to a bacterium other than the Pseudomonas KC in a site where carbon tetrachloride is to be degraded in the presence of the metabolite and the bacterium.

17. The composition of claim 16 wherein the carrier is a growth medium for the bacterium.

* * * * *